United States Patent
Ueda et al.

(10) Patent No.: US 6,362,172 B2
(45) Date of Patent: Mar. 26, 2002

(54) WATER SOLUBLE PRODRUGS OF AZOLE COMPOUNDS

(75) Inventors: Yasutsugu Ueda, Clinton; John D. Matiskella, Wallingford; Jerzy Golik, Southington; Thomas W. Hudyma, Durham; Chung-Pin Chen, Madison, all of CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 09/757,438

(22) Filed: Jan. 10, 2001

Related U.S. Application Data

(60) Provisional application No. 60/177,169, filed on Jan. 20, 2000, and provisional application No. 60/249,969, filed on Nov. 20, 2000.

(51) Int. Cl.[7] .................. A61K 31/375; C07F 9/6558
(52) U.S. Cl. .................. 514/85; 514/86; 514/93; 544/337; 544/243; 548/112
(58) Field of Search .................. 544/337, 243; 548/112; 514/85, 93, 86

(56) References Cited

U.S. PATENT DOCUMENTS

| | | | |
|---|---|---|---|
| 5,648,372 A | 7/1997 | Naito et al. | 514/383 |
| 5,707,977 A | 1/1998 | Heeres et al. | 514/85 |
| 5,714,490 A | * 2/1998 | Saksena et al. | 514/252 |
| 5,883,097 A | 3/1999 | Lovey et al. | 514/252 |
| 6,204,257 B1 | 3/2001 | Stella et al. | 514/130 |

FOREIGN PATENT DOCUMENTS

| | | |
|---|---|---|
| EP | 639577 A1 | 2/1995 |
| EP | 829478 A2 | 3/1998 |
| EP | 604910 B1 | 6/2000 |
| WO | WO 95/17407 | 6/1995 |
| WO | WO 95/19983 | 7/1995 |
| WO | WO 96/38443 | 12/1996 |
| WO | WO 97/28169 | 8/1997 |
| WO | WO 99/38873 | 8/1999 |

OTHER PUBLICATIONS

J. Golik, et al, "Synthesis and Antitumor Evaluation of Paclitaxel Phosphonooxymethyl Ethers: A Novel Class of Water Soluble Paclitaxel Pro–Drugs," Bioorganic & Medicinal Chemistry Letters, 6(15), pp. 1837–1842, 1996.

T. W. Greene, Protective Groups in Organic Synthesis, John Wiley & Sons, 1991 (Table of Contents).

A. Zwierzak, et al, "Organophosphorus Esters–I, t–Butyl as Protecting Group in Phosphorylation Via Nucleophilic Displacement," Tetrahedron, 27, pp. 3163–3170, 1971.

\* cited by examiner

Primary Examiner—Emily Bernhardt
(74) Attorney, Agent, or Firm—David M. Morse

(57) ABSTRACT

Water-soluble prodrugs of triazole antifungal compounds having a secondary or tertiary hydroxy group are provided. More particularly, new water-soluble triazole antifungal compounds are provided having the general formula

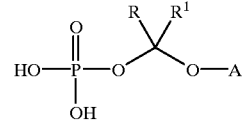

I wherein A is the non-hydroxy portion of a triazole antifungal compound of the type containing a secondary or tertiary hydroxyl group and R and $R^1$ are as defined in the specification.

18 Claims, No Drawings

WATER SOLUBLE PRODRUGS OF AZOLE COMPOUNDS

This application claims the benefit of U.S. Provisional Patent Application No. 60/177,169 filed Jan. 20, 2000 and U.S. Provisional Patent Application No. 60/249,969 filed Nov. 20, 2000.

BACKGROUND OF THE INVENTION

This invention relates to novel water-soluble azole compounds useful for the treatment of serious systemic fungal infections and suitable for both oral and, particularly, parenteral administration. More particularly, the invention relates to novel water-soluble prodrugs having the general formula:

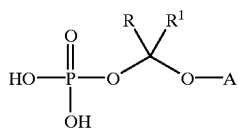

I wherein A is the non-hydroxy portion of a triazole antifungal compound of the type containing a secondary or tertiary hydroxy group, R and $R^1$ are each independently hydrogen or $(C_1-C_6)$alkyl, or pharmaceutically acceptable salts thereof.

DESCRIPTION OF THE PRIOR ART

Triazole antifungal compounds are well known in the prior art. Of the several classes known, one particularly potent class contains a tertiary hydroxyl group. For example, U. S. Pat. No. 5,648,372 discloses that (2R,3R)-3-[4-(4-cyanophenyl)thiazol-2-yl]-2-(2,4-difluorophenyl)-1-(1H-1,2,4-triazol-1-yl)-butan-2-ol has anti-fungal activity.

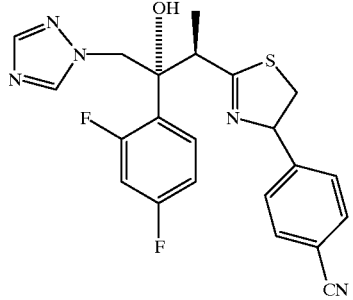

The utility of this class of compounds is limited by their low water solubility. For example, the solubility of the above triazole compound in water at pH 6.8 is 0.0006 mg/mL. This greatly impedes developing suitable parenteral dosage forms.

One method of addressing this problem was disclosed in European Patent Application 829478, where the water solubility of an azole antifungal agent was increased by attaching a linked amino-acid to the azole portion of the molecule

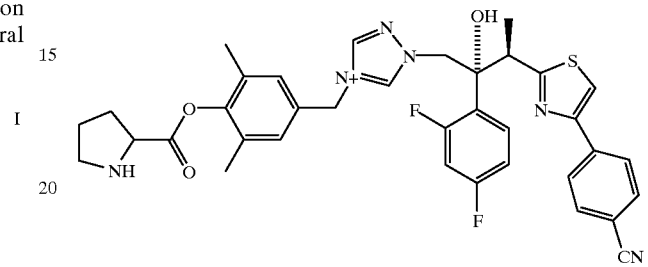

Alternatively, WO 97/28169 discloses that a phosphate moiety can be attached directly to the tertiary hydroxyl portion of the anti-fungal compound, e.g. the compound having the formula

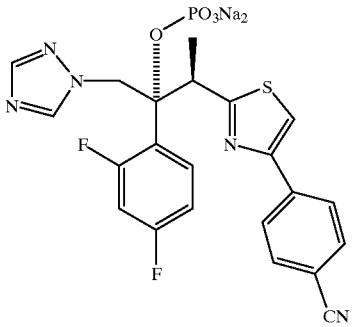

U.S. Pat. No. 5,707,977 and WO 95/19983 disclose water soluble prodrugs having the general formula

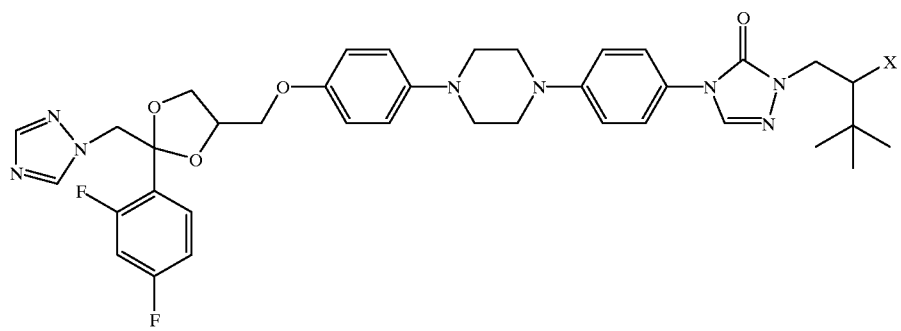

wherein X is OP(O)(OH)$_2$ or an easily hydrolyzable ester OC(O)RNR$^1$R$^2$.

WO 95/17407 discloses water-soluble azole prodrugs of the general formula

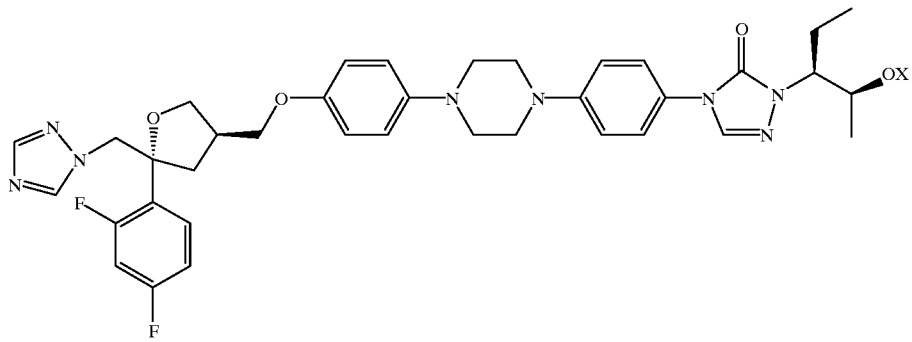

wherein X is P(O)(OH)$_2$, C(O)—(CHR$^1$)$_n$—OP(O)(OH)$_2$ or C(O)—(CHR$^1$)$_n$—(OCHR$^1$CHR$^1$)$_m$OR$_2$.

WO 96/38443 discloses water-soluble azole prodrugs of the general formula

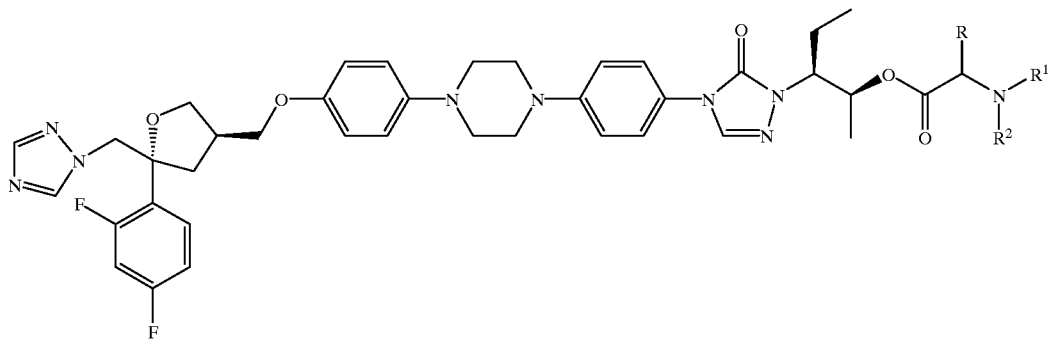

U.S. Patent No. 5,883,097 discloses water-soluble amino acid azole prodrugs such as the glycine ester

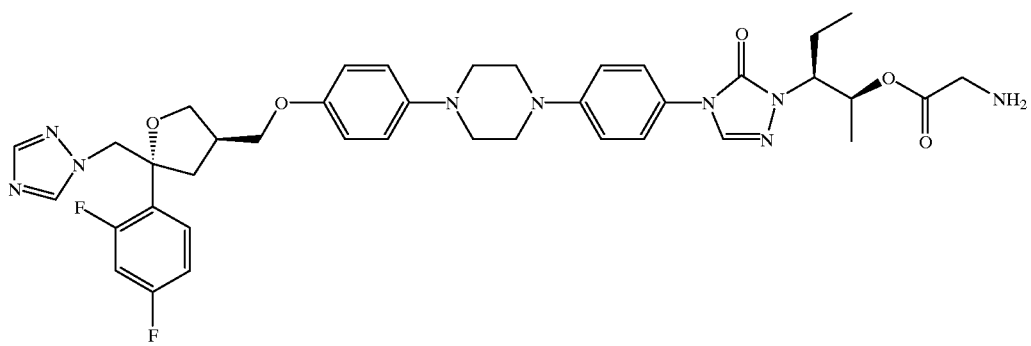

The introduction of the phosphonooxymethyl moiety into hydroxyl containing drugs has been disclosed as a method to prepare water-soluble prodrugs of hydroxyl containing drugs.

European Patent Application 604910 discloses phosphonooxymethyl taxane derivatives of the general formula

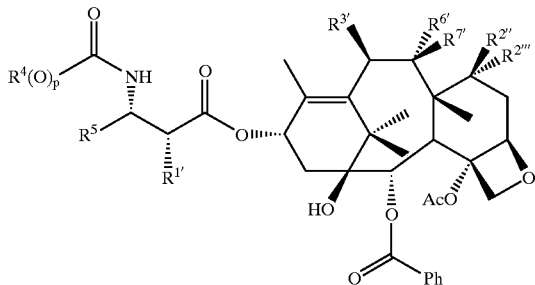

wherein at least one of $R^{1'}$, $R^{2''}$, $R^{3'}$, $R^{6'}$ or $R^{7'}$ is $OCH_2OP(O)(OH)_2$.

European Patent Application 639577 discloses phosphonooxymethyl taxane derivatives of the formula T-[OCH$_2$(OCH$_2$)$_m$OP(O)(OH)$_2$]$_n$ wherein T is a taxane moiety bearing on the C13 carbon atom a substituted 3-amino-2-hydroxypropanoyloxy group; n is 1, 2 or 3; m is 0 or an integer from 1 to 6 inclusive, and pharmaceutically acceptable salts thereof.

WO 99/38873 discloses O-phosphonooxymethyl ether prodrugs of a diaryl 1,3,4-oxadiazolone potassium channel opener.

Golik, J. et al, *Bioorganic & Medicinal Chemistry Letters,* 1996, 6:1837–1842 discloses novel water soluble prodrugs of paclitaxel such as

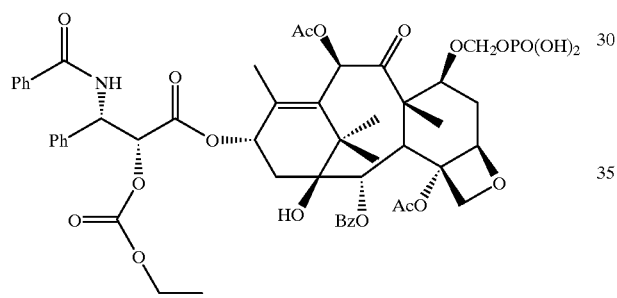

SUMMARY OF THE INVENTION

It has now been found that triazole anti-fungal compounds containing a secondary or tertiary hydroxyl group, including (2R,3R)-3-[4-(4-cyanophenyl)thiazol-2-yl]-2-(2,4-difluorophenyl)-1-(1 H-1,2,4-triazol-1-yl)-butan-2-ol, may be converted into prodrugs with superior properties to those previously disclosed by attaching a phosphate containing moiety via a linking group. Specifically, the invention covers compounds of the formula:

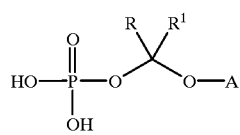

I wherein A is the non-hydroxy portion of a triazole antifungal compound of the type containing a secondary or tertiary hydroxy group, R and $R^1$ are each independently hydrogen or (C$_1$–C$_6$) alkyl, or pharmaceutically acceptable salts thereof.

The compounds of general formula I function as "prodrugs" when administered in vivo, being converted to the biologically active parent azole in the presence of alkaline phosphatase.

Preferred among the compounds of formula I are those wherein R and $R^1$ are both hydrogen.

In a preferred embodiment, A represents the non-hydroxy portion of a triazole antifungal compound of the type containing a tertiary hydroxy group.

In a more preferred embodiment of the above type compounds, A can be

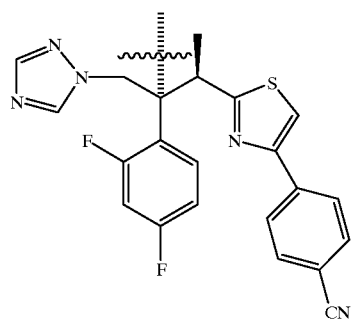

wherein $R^3$ represents phenyl substituted by one or more (preferably 1–3) halogen atoms;

$R^4$ represents H or CH$_3$;

$R^5$ represents H, or taken together with $R^4$ may represent =CH$_2$;

$R^6$ represents a 5- or 6 membered nitrogen containing ring which may be optionally substituted by one or more groups selected from halogen, =O, phenyl substituted by one or more groups selected from CN, (C$_6$H$_4$)—OCH$_2$CF$_2$CHF$_2$ and CH=CH-(C$_6$H$_4$)-OCH$_2$CF$_2$CHF$_2$, or phenyl substituted by one or more groups selected from halogen and methylpyrazolyl.

Nitrogen containing heterocycles which $R^6$ may represent include triazolyl, pyrimidinyl, and thiazolyl.

Specific examples of A include, but are not limited to, the following:

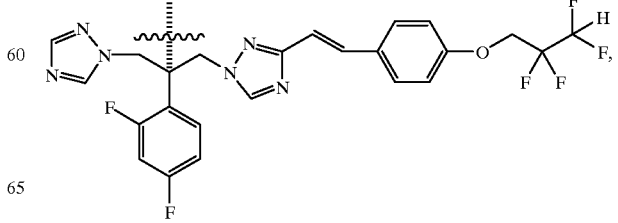

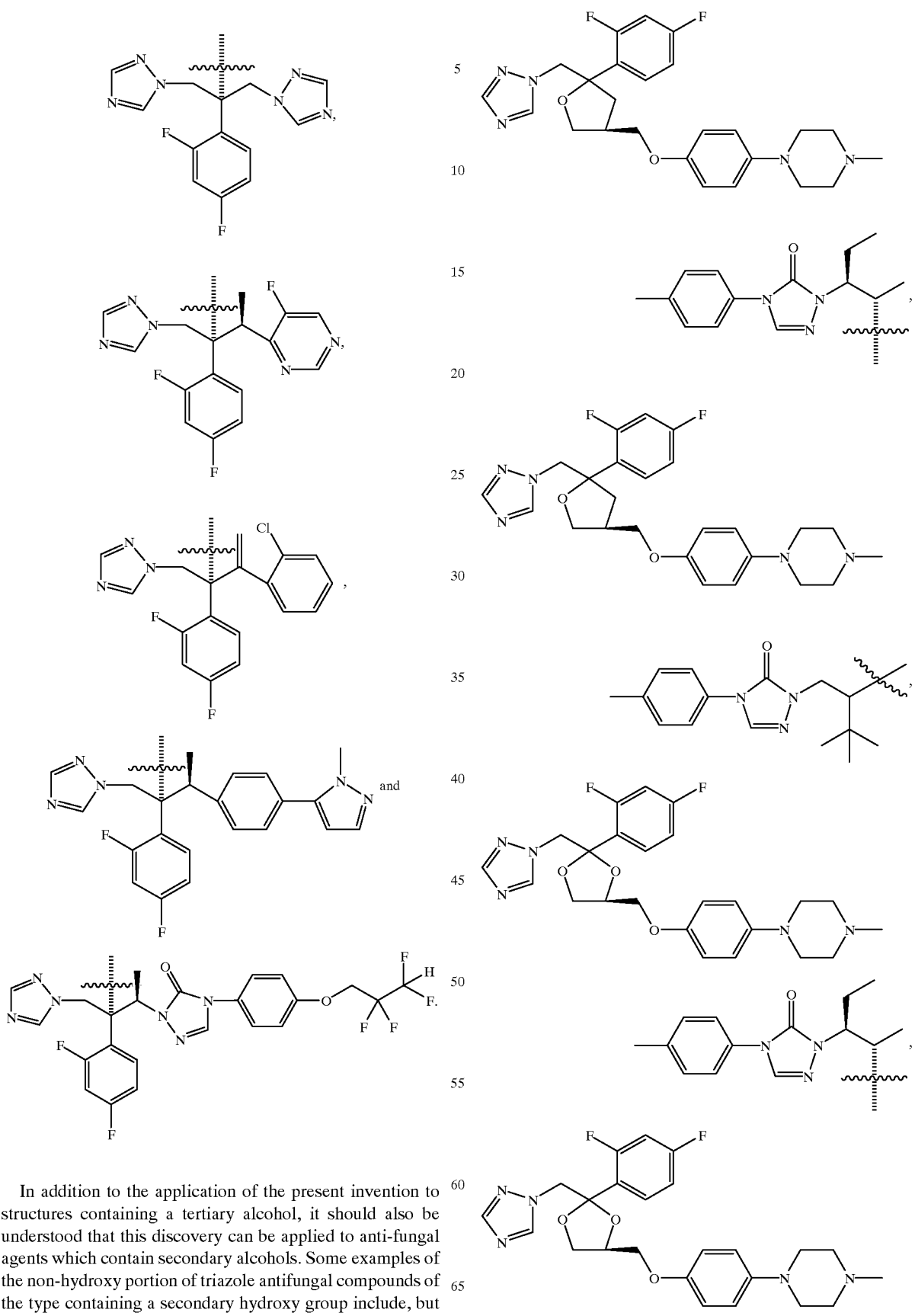

In addition to the application of the present invention to structures containing a tertiary alcohol, it should also be understood that this discovery can be applied to anti-fungal agents which contain secondary alcohols. Some examples of the non-hydroxy portion of triazole antifungal compounds of the type containing a secondary hydroxy group include, but are not limited to, the following:

-continued

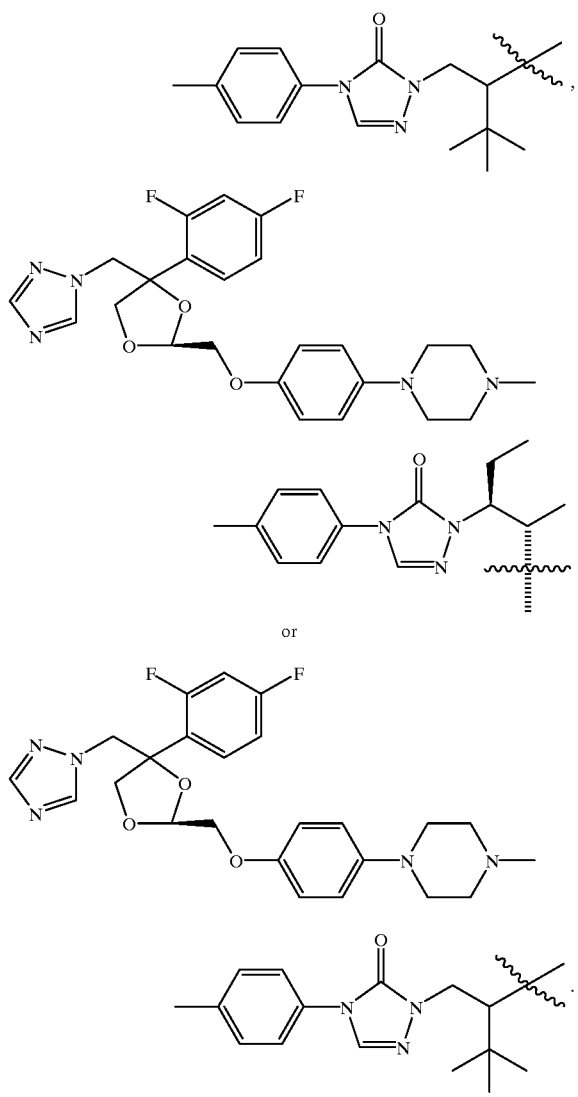

or

DETAILED DESCRIPTION

As used herein "$(C_1-C_6)$alkyl" refers to a straight or branched chain saturated aliphatic group having 1 to 6 carbon atoms such as methyl, ethyl, n-propyl, isopropyl, n-butyl, sec-butyl, t-butyl, n-pentyl, n-hexyl, etc.

The term "pharmaceutically acceptable salt" as used herein is intended to include phosphate salts with such counterions as ammonium, metal salts, salts with amino acids, salts with amines and salts with other bases such as piperidine or morpholine. Both mono- and bis-salts are intended to be encompassed by the term "pharmaceutically acceptable salts". Specific embodiments include ammonium, sodium, calcium, magnesium, cesium, lithium, potassium, barium, zinc, aluminum, lysine, arginine, histidine, methylamine, ethylamine, t-butylamine, cyclohexylamine, N-methylglucamine, ethylenediamine, glycine, procaine, benzathene, diethanolamine, triethanolamine, piperidine and morpholine. For the most preferred embodiment, (2R,3R)-3-[4-(4-cyanophenyl) thiazol-2-yl]-2-(2,4-difluorophenyl)-1-(1H-1,2,4-triazol-1-yl)-2-[(dihydrogen phosphonoxy)methoxy]butane, the t-butylamine and lysine salts are especially preferred as they can be obtained as single polymorph crystalline solids of high purity with good solubility and stability.

The term "halogen" as used herein includes chloro, bromo, fluoro and iodo, and is preferably chloro or fluoro, and most preferably fluoro.

The compounds of the present invention can be solvated or non-solvated. A preferred solvate is a hydrate.

A most preferred embodiment of the present invention is (2R,3R)-3-[4-(4-cyanophenyl)thiazol-2-yl]-2-(2,4-difluorophenyl)-1-(1H-1,2,4-triazol-1-yl)-2-[(dihydrogen phosphonoxy)methoxy]butane or a pharmaceutically acceptable salt thereof. This prodrug exhibits much improved aqueous solubility (>10 mg/mL at pH 7, 5–6 mg/mL at pH 4.3) compared with the parent compound which enables it to be used for parenteral administration as well as oral administration. This compound is also stable in solution, can be isolated in crystalline form and is readily converted to parent drug in vivo.

The compounds of the present invention may be made by the following general reaction scheme. In this method, A represents the non-hydroxy portion of a triazole antifungal compound of the type containing a tertiary or secondary hydroxyl group, Pr represents a conventional hydroxy-protecting groups such as t-butyl, benzyl or allyl, and R and $R^1$ are each independently hydrogen or $(C_1-C_6)$alkyl. Most preferably, R and $R^1$ are both hydrogen.

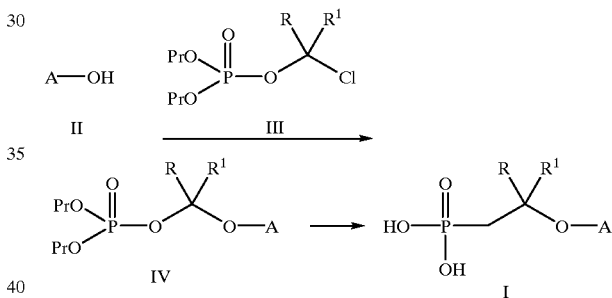

To elaborate on the method, the antifungal parent compound of interest, II, is converted into the phosphate intermediate IV by O-alkylation with chloride intermediate III in the presence of a suitable base such as sodium hydride, potassium hydride, sodium amide, sodium t-butoxide, potassium t-butoxide, sodium bis(trimethylsilyl)amide, potassium bis(trimethylsilyl)amide, or combinations thereof such as sodium hydride plus sodium bis(trimethylsilyl)amide. This reaction step may be carried out in an inert organic solvent such as tetrahydrofuran, methyl-tetrahydrofuran, methyl t-butyl ether, diethylether or dimethylacetamide at a temperature of from about 0° to 50° C., more preferably between about 20° to 40° C., and most preferably at about 40° C. The most preferred base is sodium hydride and the most preferred solvent is tetrahydrofuran. The most preferred R and $R^1$ groups are hydrogen.

Ester intermediate IV is then subjected to a conventional deprotection step to remove the hydroxyl-protecting groups Pr. The reagents used in such step will depend on the particular hydroxyl-protecting group used, but will be well known to those skilled in the art. The most preferred hydroxy protecting group is the t-butyl group which can be removed with trifluoroacetic acid, hydrochloric acid or formic acid in an appropriate inert organic solvent. The inert solvent may be, for example, methylene chloride, dichloroethane, methylbenzene or trifluoromethyl benzene. In the case of the preferred deprotection step with the di-tertiary butyl ester, it is preferred to do the deprotection step in trifluoroacetic acid in methylene chloride at a temperature of from about 0° to 40° C., most preferably at a temperature of about 0–5° C.

The final product I may then be recovered and purified by conventional procedures such as reverse phase C-18 column chromatography or solvent extraction.

End product I may, of course, be converted by conventional means to a desired pharmaceutically acceptable salt as described above.

It was later discovered that use of purified reagent III gave fairly low yields of intermediate IV (approximately 10–35% yield) in the above reaction, resulting in low overall yields of product I. However, when a source of iodide ion is added to the O-alkylation step of the above reaction, the yield of intermediate IV is unexpectedly increased to up to about 90%, thus also significantly increasing the yield of final product I. It is believed that the addition of the iodide ion may result in in situ formation of the corresponding iodide intermediate III' of the formula

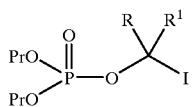

III' and that use of this reagent results in a large increase in yield of the phosphate intermediate IV. The attempt to substitute preformed intermediate III' directly for intermediate III in the first step of the above reaction, however, was unsuccessful due to the greatly decreased stability of iodide reagent III' compared to the chloride intermediate III. An alternative method which was successful involves using iodine in the O-alkylation step along with chloride intermediate III in the presence of base such as NaH (which also may act as a reducing agent for the iodine). It is believed that the iodine is reduced to iodide ion which then converts chloride intermediate III in situ to iodide intermediate III' to facilitate this step of the process. The illustrative example below shows the O-alkylation step using elemental iodine which is the preferred method of carrying out this reaction to get intermediate IV.

By forming the iodide reagent III' in situ by addition of a source of iodide ion or by reaction of iodine and reagent III in the presence of strong base, the greatly increased yield of phosphate ester IV allows the final product I to be also obtained in greatly increased yield.

The source of iodide ion is preferably sodium iodide, but may also include lithium iodide, cesium iodide, cadmium iodide, cobalt iodide, copper iodide, rubidium iodide, barium iodide, zinc iodide and calcium iodide. About 2–3 equivalents of the iodide salt is generally used per equivalent of parent compound A—OH.

When elemental iodine is used in the coupling step, about 0.1 to 1.0 equivalent of iodine, preferably 0.5 equivalent, is employed per equivalent of parent compound A—OH.

The bases and solvents which are used when iodine or iodide ion is used are the same as those described above when reagent III is used per se.

It will be understood that where the substituent groups used in the above reactions contain certain reaction sensitive functional groups such as amino or carboxylate groups which might result in undesirable side-reactions, such groups may be protected by conventional protecting groups known to those skilled in the art. Suitable protecting groups and methods for their removal are illustrated, for example, in *Protective Groups in Organic Synthesis,* Theodora W. Greene (John Wiley & Sons, 1991). It is intended that such "protected" intermediates and end-products are included within the scope of the present disclosure and claims.

It will be appreciated that certain products within the scope of formula I may have substituent groups which can result in formation of optical isomers. It is intended that the present invention include within its scope all such optical isomers as well as epimeric mixtures thereof, i.e. R- or S- or racemic forms.

The pharmaceutically active compounds of this invention may be used alone or formulated as pharmaceutical compositions comprising, in addition to the active triazole ingredient, a pharmaceutically acceptable carrier, adjuvant or diluent. The compounds may be administered by a variety of means, for example, orally, topically or parenterally (intravenous or intramuscular injection). The pharmaceutical compositions may be in solid form such as capsules, tablets, powders, etc. or in liquid form such as solutions, suspensions or emulsions. Compositions for injection may be prepared in unit dose form in ampules or in multidose containers and may contain additives such as suspending, stabilizing and dispersing agents. The compositions may be in ready-to-use form or in powder form for reconstitution at the time of delivery with a suitable vehicle such as sterile water.

Alternatively, the compounds of the present invention can be administered in the form of a suppository or pessary, or they may be applied topically in the form of a lotion, solution, or cream. Additionally, they may be incorporated (at a concentration up to 10%) into an ointment consisting of a white wax or soft, white paraffin base together with the required stabilizers and/or preservatives.

The compounds of the invention are useful because they possess pharmacological activities in animals, including particularly mammals and most particularly, humans. Specifically, the compounds of the present invention are useful for the treatment or prevention of topical fungal infections, including those caused by species of Candida, Trichophyton., Microsporum, or Epidermophyton. Additionally, they are useful for the treatment of mucosal infections caused by *Candida albicans.* They can also be used in the treatment of systemic fungal infections caused, for example, by species of *Candida albicans, Cryptococcus neoformans, Aspergillus flavus, Aspergillus fumigatus,* Coccidioides, Paracoccidiodes, Histoplasma, or Blastomyces.

Thus, according to another aspect of the invention, there is provided a method of treating a fungal infection which comprises administering a therapeutically effective amount of the compound to a host, particularly a mammalian host and most particularly a human patient. The use of the compounds of the present invention as pharmaceuticals and the use of the compounds of the invention in the manufacture of a medicament for the treatment of fungal infections are also provided.

The dosage to be administered depends, to a large extent, on the particular compound being used, the particular composition formulated, the route of administration, the nature and condition of the host and the particular situs and organism being treated. Selection of the particular preferred dosage and route of application, then, is left to the discretion of the physician or veterinarian. In general, however, the compounds may be administered parenterally or orally to mammalian hosts in an amount of from about 5 mg/day to about 1.0 g/day. These doses are exemplary of the average case, and there can be individual instances where higher or lower dosages are merited, and such dosages are within the scope of this invention. Furthermore, administration of the compounds of the present inventions can be conducted in either single or divided doses.

The in vitro evaluation of the antifungal activities of the compounds of the invention can be performed by determining the minimum inhibitory concentration (MIC). The MIC is the concentration of test compound which inhibits the growth of the test microorganism. In practice, a series of agar plates, each having the test compound incorporated at a specific concentration, is inoculated with a fungal strain and each plate is then incubated for 48 h at 37° C. The plates are examined for the presence or absence of fungal growth, and the relevant concentration is noted. Microorganisms which can be used in the test include *Candida albicans, Asperigillus fumigatus,* Trichophyton spp., Microsporum spp. *Epidermophyton floccosum, Coccidioides immitis,* and *Torulopsos galbrata.* It should be recognized that, as prodrugs, some compounds of the invention may not be active in the in vitro test.

The in vivo evaluation of compounds of the present invention can be carried out at a series of dose levels by intraperitoneal or intravenous injection or by oral administration to mice which have been inoculated with a strain of fungus (e.g. *Candida albicans*). Activity is determined by comparing the survival of the treated group of mice at different dosage levels after the death of an untreated group of mice. The dose level at which the test compound provides 50% protection against the lethal effect of the infection is noted.

The compounds of the present invention substantially increase the solubility of the parent triazole antifungal compound and also release the bioactive parent compound (i.e. function as a prodrug) as demonstrated in human liver S9 experiments.

ILLUSTRATIVE EXAMPLES

The following examples illustrate the invention, but are not intended as a limitation thereof. The abbreviations used in the examples are conventional abbreviations well-known to those skilled in the art. Some of the abbreviations used are as follows:

| | | |
|---|---|---|
| h | = | hour(s) |
| rt | = | room temperature |
| mmol | = | mmole(s) |
| g | = | gram(s) |
| THF | = | tetrahydrofuran |
| mL | = | milliliter(s) |
| L | = | liter(s) |
| Et$_2$O | = | diethyl ether |
| EtOAc | = | ethyl acetate |
| TFA | = | trifluoroacetic acid |
| CH$_2$Cl$_2$ | = | dichloromethane |
| CH$_3$CN | = | acetonitrile |

In the following examples, all temperatures are given in degrees Centigrade. Melting points were determined on an electrothermal apparatus and are not corrected. Proton nuclear magnetic resonance ($^1$H NMR) spectra were recorded on a Bruker –500, Bruker AM–300 or a Varian Gemini 300 spectrometer. All spectra were determined in CDCl$_3$ or D$_2$O unless otherwise indicated. Chemical shifts are reported in δ units (ppm) relative to tetramethylsilane (TMS) or a reference solvent peak and interproton coupling constants are reported in Hertz (Hz). Splitting patterns are designated as follows: s, singlet; d, doublet; t, triplet; q, quartet; m, multiplet; br, broad peak; dd, doublet of doublets; dt, doublet of triplets; and app d, apparent doublet, etc. Mass spectra were recorded on a Kratos MS-50 or a Finnegan 4500 instrument utilizing direct chemical ionization (DCI, isobutene), fast atom bombardment (FAB), or electron ion spray (ESI).

Analytical thin-layer chromatography (TLC) was carried out on precoated silica gel plates (60F-254) and visualized using UV light, iodine vapors, and/or staining by heating with methanolic phosphomolybdic acid. Reverse phase chromatography was performed in a glass column using C18 silica gel (Waters Corporation Preparative C18 125A) at pressures somewhat above atmospheric pressure.

EXAMPLE 1

(2R,3R)-3-[4-(4-cyanophenyl)thiazol-2-yl]-2-(2,4-difluorophenyl)-1-(1H-1,2,4-triazol-1-yl)-2-[(dihydrogen phosphonoxy)methoxy]butane, sodium salt

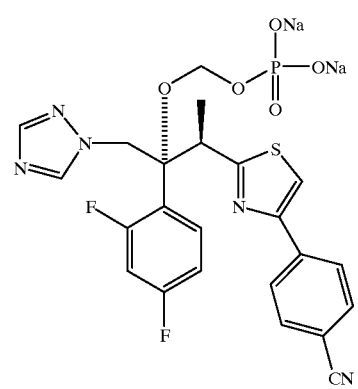

I (2R,3R)-3-[4-(4-cyanophenyl)thiazol-2-yl]-2-(2,4-difluorophenyl)-1-(1H-1,2,4-triazol-1-yl)-2-[(di-tert-butyl phosphonoxy)methoxy]butane

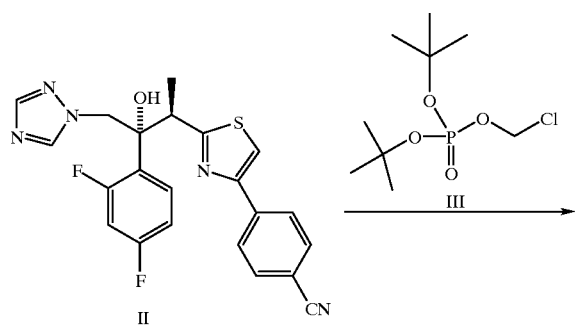

-continued

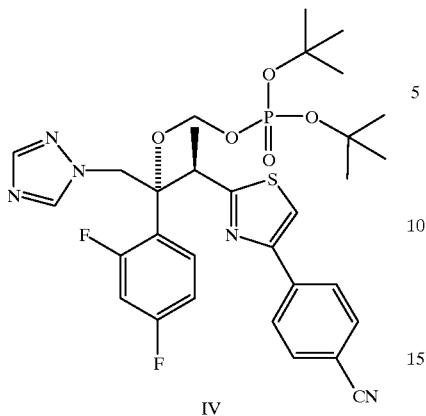

IV

To a solution of (2R,3R)-3-[4-(4-cyanophenyl)thiazol-2-yl]-2-(2,4-difluorophenyl)-1-(1H-1,2,4-triazol-1-yl)butan-2-ol, II, (8.74 g, 20 mmol) in THF (40 mL) under a nitrogen atmosphere was added sodium hydride (0.80 g, 60% in oil, 20 mmol) at rt. The resulting mixture was stirred at rt for 0.25 h and then di-tert -butyl chloromethyl phosphate, III, (10.3 g, 40 mmol) was added. The reaction mixture was heated at 50° C. for 16 h. The reaction mixture was then allowed to cool to rt and was concentrated under reduced pressure. The residue was dissolved in $Et_2O$ and was washed with $H_2O$ and brine. The organic layer was dried over $MgSO_4$ and was concentrated under reduced pressure to obtain 17.0 g of crude subtitled compound, IV, as a gum. A small portion of this crude compound was purified by reverse phase chromatography on C-18. The column was eluted with 30% $CH_3CN/H_2O$, 38% $CH_3CN/H_2O$, 45% $CH_3CN/H_2O$ and then 50% $CH_3CN/H_2O$. The product containing fractions were concentrated under reduced pressure in order to remove $CH_3CN$. The resulting aqueous layer was then extracted with $Et_2O$. The $Et_2O$ layers were washed with brine, dried and concentrated under reduced pressure to afford purified subtitled compound, IV, as a white solid. $^1$H NMR (300 MHz, $CDCl_3$): δ8.35 (s, 1H), 7.98 (d, 2H, J=9), 7.76 (s, 1H), 7.71 (d, 2H, J=9), 7.63 (s, 1H), 7.36–7.27 (m, 1H), 6.86–6.78 (m, 2H), 5.53 (dd, 1H, J=28,6), 5.53 (dd, 1H, J=9,6), 5.17 (d, 1H, J=15), 5.03 (d,1H, J=15), 4.01 (q, 1H, J=7), 1.47 (s, 9H), 1.45 (s, 9H), 1.37 (d, 3H, J=7). MS [ESI$^{30}$ (M+H)$^+$]660.2 obs.

B. (2R,3R)-3-[4-(4-cyanophenyl)thiazol-2-yl]-2-(2,4-difluorophenyl)-1-(1H-1,2,4-triazol-1-yl)-2-[(dihydrogen phosphonoxy)methoxy]butane, sodium salt

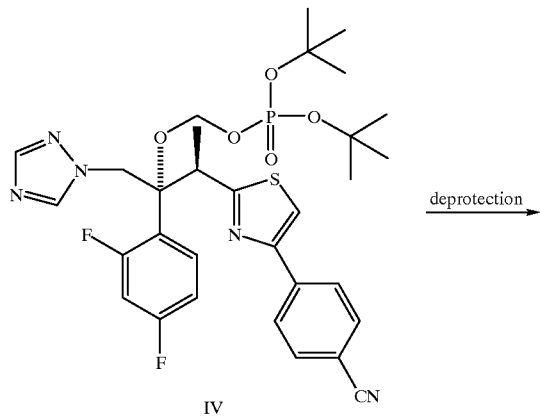

-continued

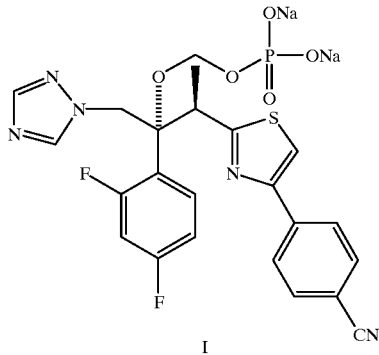

I

The crude (2R,3R)-3-[4-(4-cyanophenyl)thiazol-2-yl]-2-(2,4-difluorophenyl)-1-(1H-1,2,4-triazol-1-yl)-2-[(di-tert-butyl phosphonoxy)methoxy]butane, IV, (17 g) was dissolved in $CH_2Cl_2$ (100 mL). To this solution was added TFA (50 mL) and the reaction mixture was stirred at rt for 0.25 h. The reaction mixture was then concentrated under reduced pressure. To the residue was added $H_2O$ (200 mL), $Et_2O$ (100 mL) and EtOAc (100 mL). The pH of the aqueous layer was adjusted to 7.6 by addition of solid $Na_2CO_3$ and then the organic and aqueous layers were separated. The aqueous layer was then subjected to reverse phase chromatography on 400 g of C-18 eluted with $H_2O$ to 5% $CH_3CN/H_2O$. The product containing fractions were concentrated under reduced pressure, frozen and lyophilized to afford 1.5 g of the subtitled compound, I, as a white solid. (1.5 g, 12% over two steps). $^1$H NMR (500 MHz, $D_2O$) δ8.91 (s, 1H), 7.92 (s, 1H),. 7.81 (d, 2H, J=8), 7.80 (s, 1H), 7.77 (d, 2H, J=8), 7.21 (dd, 1H, J=15,9), 6.99 (ddd, 1H, J=9,9,2), 6.91 (ddd, 1H, J=9,9,2), 5.35 (dd, 1H, J=6,6), 5.29 (d, 1H, J=15), 5.21 (dd, 1H, J=6,6), 5.19 (d, 1H, J=15), 3.86 (q, 1H, J=7), and 1.35 (d, 3H, J=7); MS [(ESI$^{31}$ (M-H)$^{31}$ 546.1]; Anal. Calcd for $C_{23}H_{18}F_2N_5O_5S_1P_1/Na_2/3.5\ H_2O$: C, 42.21: H, 3.85: N, 10.70: Na, 7.03. found: C, 42.32: H, 3.83: N, 10.60: Na, 7.04.

Di-tert-butyl chloromethyl phosphate, III:

Di-tert-butyl chloromethyl phosphate, III, may be made by any of the following methods.

Method 1

Silver di-t-butyl phosphate (6.34 g, 20 mmol), which was prepared by mixing di-t-butyl phosphate (obtained from di-t-butyl phosphite by the method of Zwierzak and Kluba, Tetrahedron, 1971, 27, 3163) with one equivalent of silver carbonate in 50% aqueous acetonitrile and by lyophilizing to dryness, was placed together with chloroiodomethane (35 g, 200 mmol) in benzene and stirred at room temperature for 18 hrs. The reaction mixture was filtered and the filtrate concentrated under reduced pressure. The residue was chromatographed on silica and eluted with 2:1 hexanes-ethyl acetate. Appropriate fractions were concentrated to dryness to obtain the subtitled compound III (3.7 g, 71% yield): $^1$H NMR ($CDCl_3$) δ65.63 (d, 2H, J=17), 1.51 (s, 18H); MS (MH$^+$=259).

Method 2

Tetrabutylammonium di-t-butyl phosphate was prepared by dissolving di-t-butyl phosphate [20g, 94 mmol (obtained from di-t-butyl phosphite by the method of Zwierzak and Kluba, Tetrahedron, 1971, 27, 3163)] in methanolic tetrabutylammonium hydroxide (47 mL of 1M solution, 47 mmol). The reaction mixture had a temperature of 23° C. and pH of 4.33. The pH of the reaction mixture was adjusted to 6.5–7.0 by addition of methanolic tetrabutylammonium hydroxide (48 mL of 1M solution, 48 mmol) over 0.2 h. The reaction mixture was stirred for 0.5 h at approximately 26° C. and then was concentrated under reduced pressure at a bath temperature below 40° C. The crude residue was azeotroped three times by adding toluene (3×100 mL) and then the mixture was concentrated under reduced pressure. The crude residue was then triturated in cold hexanes (0° C.) for 1 h and then the solid was collected by filtration, washed with a minimum amount of cold hexanes and dried to give a first crop of tetrabutylammonium di-t-butyl phosphate as a white solid. (24.0 g). The mother liquor was concentrated under reduced pressure and then triturated in cold hexanes (20 mL) for 1 h. The solid was collected by filtration, washed with a minimum amount of cold hexanes and dried to give a second crop of tetrabutylammonium di-t-butyl phosphate as a white solid. [(8.5 g), 32.5 g total (77%)]. A solution of tetrabutylammonium di-t-butyl phosphate (218 g, 480 10 mmol) in benzene (200 mL) was added dropwise to stirred chloroiodomethane (800 g, 4535 mmol) over 1.5 h at rt. The reaction mixture was stirred an additional 1.5 h at rt and then was concentrated under reduced pressure. The oily residue was dissolved in $Et_2O$ and filtered to remove white solids which had precipitated. The organic layer was washed with saturated $NaHCO_3$ and $H_2O$ brine (1/1). The organic layer was then dried over magnesium sulfate, filtered and concentrated under reduced pressure to yield a red brown oil (320 g). The red brown oil was subjected to chromatography on silica gel (800 g) eluted with 20% EtOAc/Hexanes, 25% EtOAc/Hexanes then 30% EtOAc/Hexanes. The product containing fractions were concentrated under reduced pressure to yield a golden oil. The oil was diluted with $CH_2Cl_2$ (30 mL), concentrated under reduced pressure and then dried under vacuum to yield the subtitled compound III (61.3 g, 49% yield). $^1$H NMR (Benzene-$d_6$) δ5.20 (2H, d, J=15), 1.22 (18H, s).

Method 3

Iodochloromethane (974 g, 402 mL, 5.53 mol) at 25° C. was treated with tetrabutylammonium di-t-butylphosphate (250 g, 0.553 mol). The phosphate was added portionwise over 10 minutes. The heterogeneous mixture became a clear pink solution after approximately 15 minutes. The mixture was stirred for three hours, and the iodochloromethane was then removed by rotary evaporation with a bath temperature of <30° C. The residue was taken up in 1 L t-butyl methyl ether and stirred for 15 minutes to precipitate tetrabutylammonium iodide by-product. Tetrabutylammonium iodide was removed by vacuum filtration through a sintered glass funnel. The filtrate was concentrated by rotary evaporation to an oil which contained a 5:1 mixture of III and undesired dimer impurity

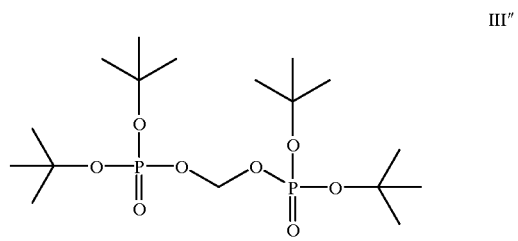

III″

The mixture can be purified by a silica gel chromatography to obtain III as pure compound in ~60% yield as an oil.

EXAMPLE 2

(2R,3R)-3-[4-(4-cyanophenyl)thiazol-2-yl]-2-(2,4-difluorophenyl)-1-(1H-1,2,4,- triazol-1-yl)-2-[(dihydrogen phosphonoxy)methoxy]butane

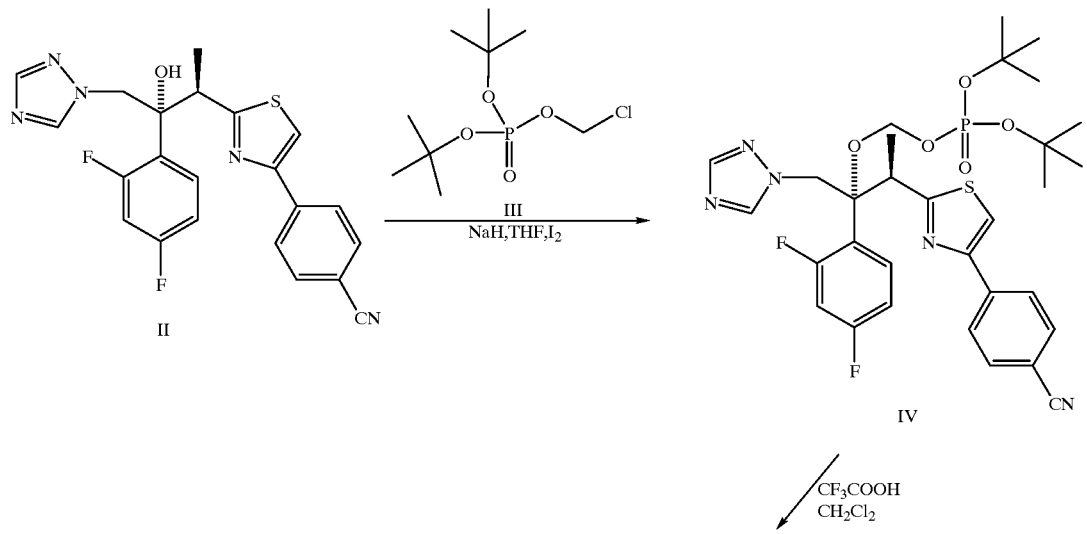

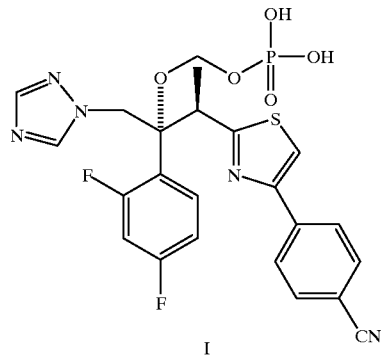

A. An oven dried, 1L round-bottom flask equipped with a mechanical stirrer, nitrogen inlet adapter, pressure-equalizing addition funnel fitted with a rubber septum and temperature probe was charged with sodium hydride (2.89 g, 0.069 mol, 60%) and THF (50 mL). To this stirred suspension, (2R,3R)-3-[4-(4-cyanophenyl)thiazol-2-yl]-2-(2,4-difluorophenyl)-1-(1H-1,2,4-triazol-1-yl)butan-2-ol, II, (10 g, 0.023 mol) in 30 mL of THF was added dropwise over 20 minutes at room temperature. After stirring for 45 minutes, a solution of iodine (2.99 g, 0.0115 mol) in THF (30 mL)) was added dropwise over 10 minutes followed by dropwise addition of compound di tert butylchloromethyl phosphate, III (13.29 g, 0.035 mol, ~68% purity) over 15 minutes. The reaction mixture was stirred for 4 hours at about 41° C. to complete the reaction. The completion of the reaction was judged by in-process HPLC. The reaction mixture was poured into ice cold water (100 mL). The aqueous phase was separated and extracted with ethyl acetate (3×50 mL) and the combined organic extract was washed with 10% sodium thiosulfite (50 mL), water (50 mL), brine (50 mL), dried over magnesium sulfate and concentrated under reduced pressure to give pale yellow oil (22.8 g, In-process HPLC: ~97% pure). The crude product was used "as is" in step B.

B. To a round-bottom flask equipped with magnetic stirrer, cooling bath, pH probe and $N_2$ inlet-outlet was charged the product of Step A above (7.5 g) in $CH_2Cl_2$ (23 mL) and cooled to 0° C. To this stirred solution, trifluoroacetic acid (8.8 mL) was added slowly and stirred for 3 h to complete the reaction. The completion of the reaction was judged by in-process HPLC. The reaction mixture was poured into a cold solution of 2N NaOH (64 mL). The reaction mixture was extracted with t-butyl acetate (2×65 mL) to remove all the organic impurities. The aqueous layer containing the title product as bis sodium salt was treated with activated charcoal (10 g) and filtered through a bed of Celite. The clear filtrate was acidified with 1N HCl to pH 2.5. The free acid, the title product, was extracted into ethyl acetate (2×50 mL). The combined organic layer was washed with water, dried over $MgSO_4$, filtered, and the filtrate concentrated under reduced pressure to afford 3.39 g of crude title product.

EXAMPLE 3

Bis lysine salt of (2R,3R)-3-[4-(4-cyanophenyl) thiazol-2-yl]-2-(2,4-difluorophenyl)-1-(1H-1,2,4-triazol-1-yl)-2-[(dihydrogen phosphonoxy)methoxy] butane The above obtained title product from Example 2 was dissolved in methanol (75 mL) and to this L-lysine (1.8 g) was added and heated at 60° C. for 4.5 h. The hot reaction mixture was filtered through a bed of Celite. The filtrate was concentrated to about 5 mL, mixed with ethanol (100 mL) and heated to 65° C. to crystallize the bis lysine salt. The salt was collected on a Buchner funnel and dried under vacuum to afford 3.71 g of the title compound as an off white crystalline solid.

EXAMPLE 4

Tert-butyl amine salt of (2R,3R)-3-[4-(4-cyanophenyl)thiazol-2-yl]-2-(2,4-difluorophenyl)-1-(1H-1,2,4-triazol-1-yl)-2-[(dihydrogen phosphonoxy)methoxy]butane A solution of title product of Example 2 was dissolved in 50 mL of ethyl acetate and to this was added t-butyl amine (5.3 mL) under nitrogen. The reaction mixture was stirred at 40° C. for about 1 hour to crystallize the product. The bis t-butyl amine salt was collected on a Buchner funnel and dried under vacuum to afford 2.21 g of the title compound as an off white crystalline solid.

We claim:

1. A compound of the formula

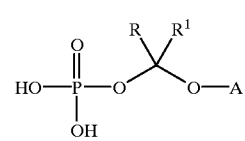

wherein A is

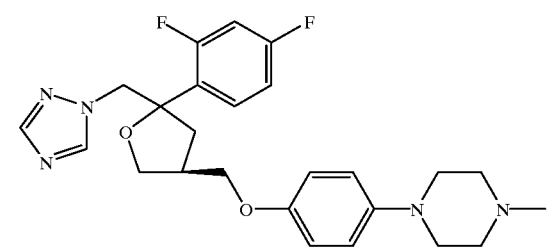

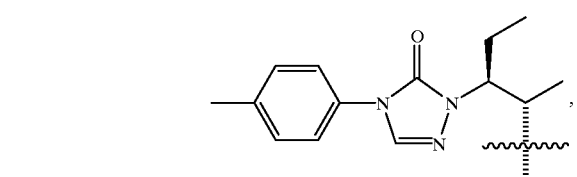

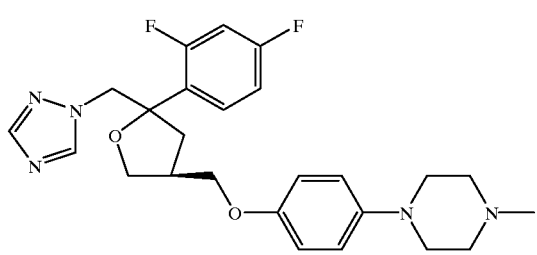

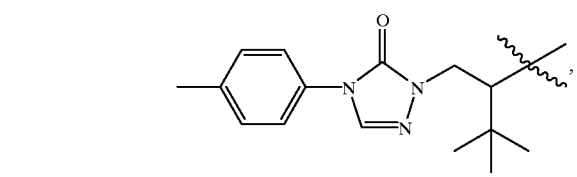

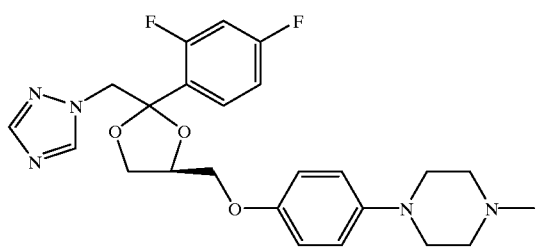

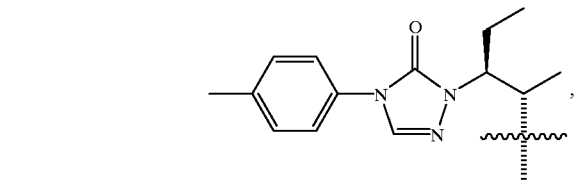

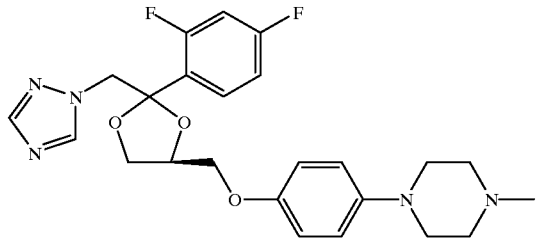

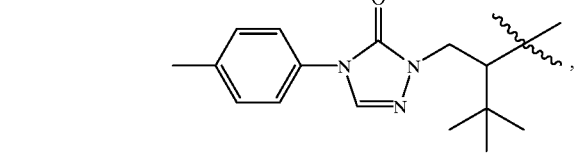

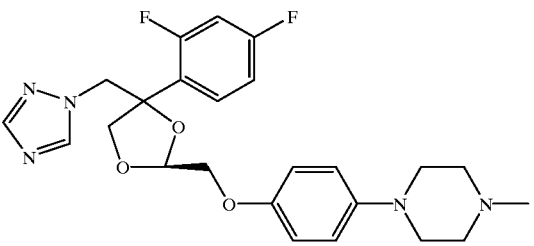

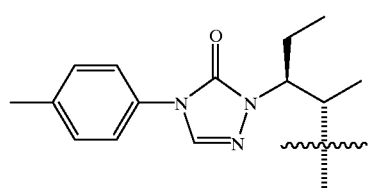

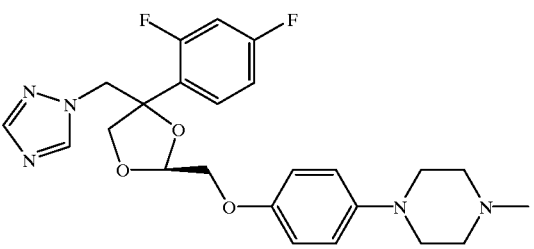

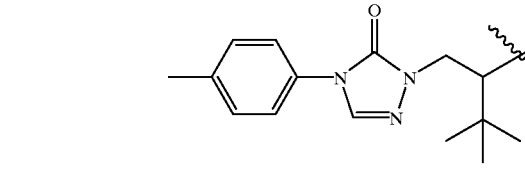

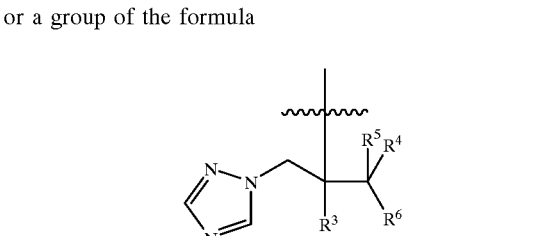

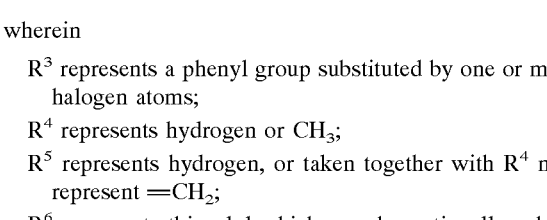

or a group of the formula

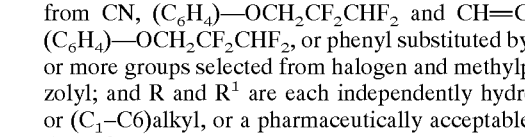

wherein $R^3$ represents a phenyl group substituted by one or more halogen atoms;

$R^4$ represents hydrogen or $CH_3$;

$R^5$ represents hydrogen, or taken together with $R^4$ may represent $=CH_2$;

$R^6$ represents thiazolyl which may be optionally substituted by one or more groups selected from halogen, $=O$, phenyl substituted by one or more groups selected from CN, $(C_6H_4)$—$OCH_2CF_2CHF_2$ and CH=CH—$(C_6H_4)$—$OCH_2CF_2CHF_2$, or phenyl substituted by one or more groups selected from halogen and methylpyrazolyl; and R and $R^1$ are each independently hydrogen or $(C_1$–$C6)$alkyl, or a pharmaceutically acceptable salt thereof.

2. A compound of claim 1 wherein A represents

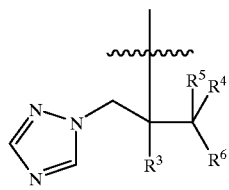

wherein
- $R^3$ represents a phenyl group substituted by one or more halogen atoms;
- $R^4$ represents hydrogen or $CH_3$;
- $R^5$ represents hydrogen, or taken together with $R^4$ may represent $=CH_2$;
- $R^6$ represents thiazolyl which may be optionally substituted by one or more groups selected from halogen, $=O$, phenyl substituted by one or more groups selected from CN, $(C_6H_4)$—$OCH_2CF_2CHF_2$ and $CH=CH$—$(C_6H_4)$—$OCH_2CF_2CHF_2$, or phenyl substituted by one or more groups selected from halogen and methylpyrazolyl.

3. A compound as claimed in claim 2 wherein $R^3$ is 2,4-difluorophenyl.

4. A compound as claimed in claim 3 wherein $R^4$ is methyl and $R^5$ is hydrogen.

5. A compound as claimed in claim 4 wherein wherein $R^6$ is 4-(4-cyanophenyl)-thiazol-2-yl.

6. A compound of claim 5 wherein R and $R^1$ are each hydrogen, or a pharmaceutically acceptable salt thereof.

7. The compound named (2R,3R)-3-[4-(4-cyanophenyl)thiazol-2-yl]-2-(2,4-difluorophenyl)-1-(1H-1,2,4-triazol-1-yl)-2-[(dihydrogen phosphonoxy)methoxy]butane, or a pharmaceutically acceptable salt thereof.

8. The crystalline bis lysine salt of (2R,3R)-3-[4-(4-cyanophenyl)thiazol-2-yl]-2-(2,4-difluorophenyl)-1-(1H-1,2,4-triazol-1-yl)-2-[(dihydrogen phenoxy)methoxy]butane.

9. The crystalline tertiary-butylamine salt of (2R,3R)-3-[4-(4-cyanophenyl)thiazol-2-yl]-2-(2,4-difluorophenyl)-1-(1H-1,2,4-triazol-1-yl)-2-[(dihydrogen phenoxy)methoxy]butane.

10. A compound of claim 1 wherein A is

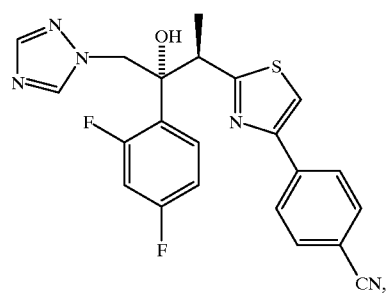

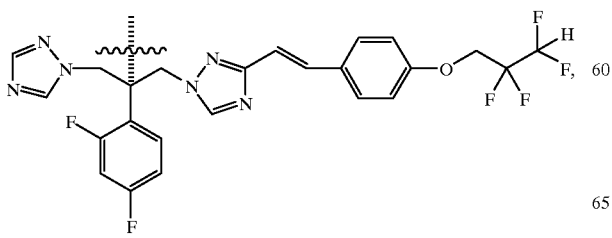

-continued

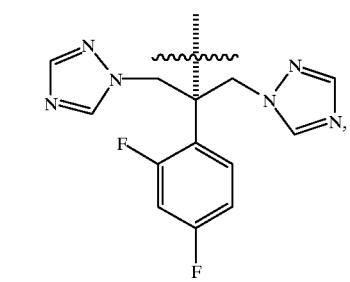

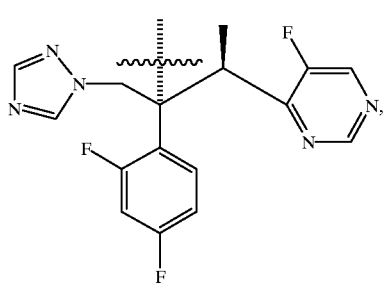

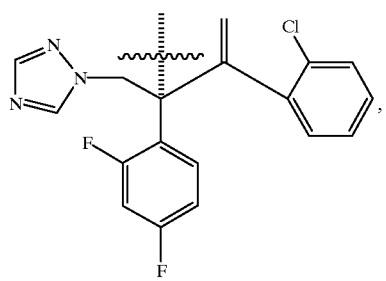

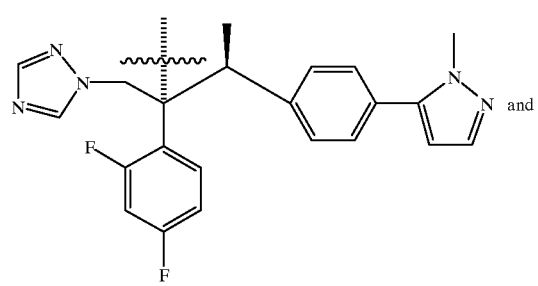

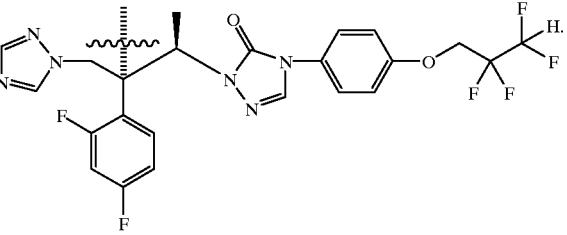

11. A compound of the formula

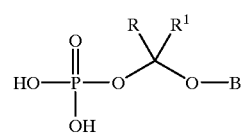

IA wherein B is

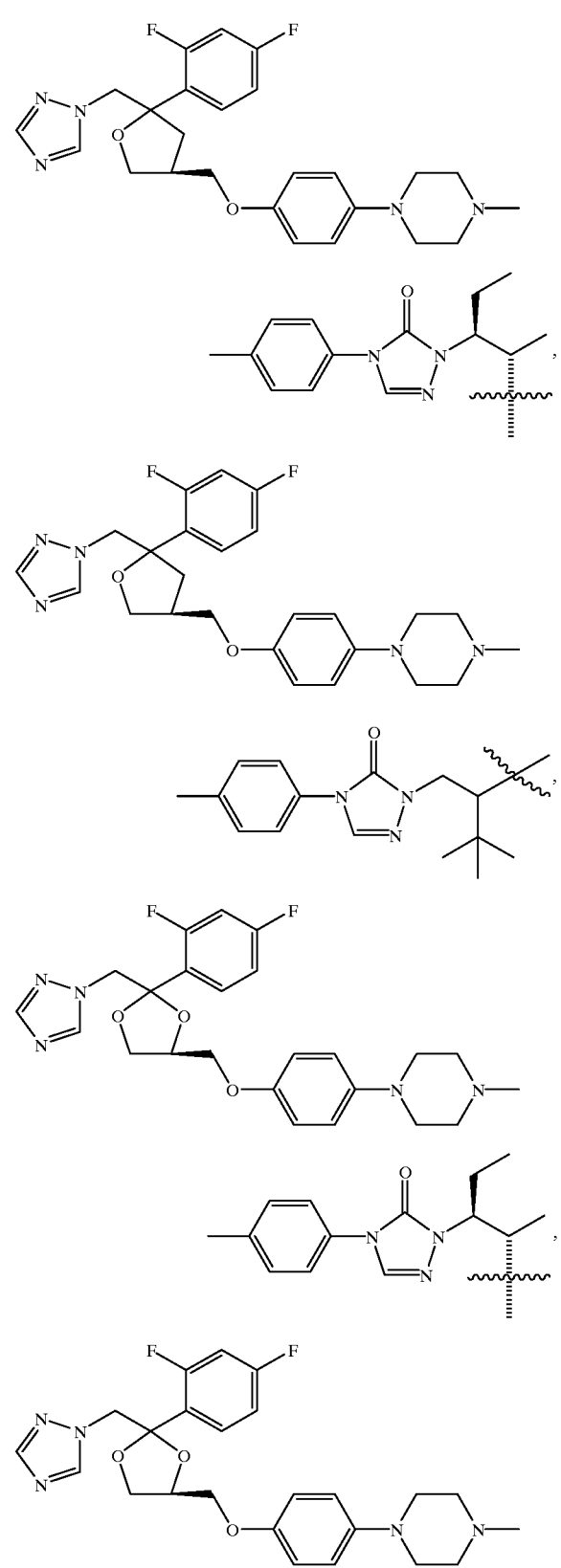

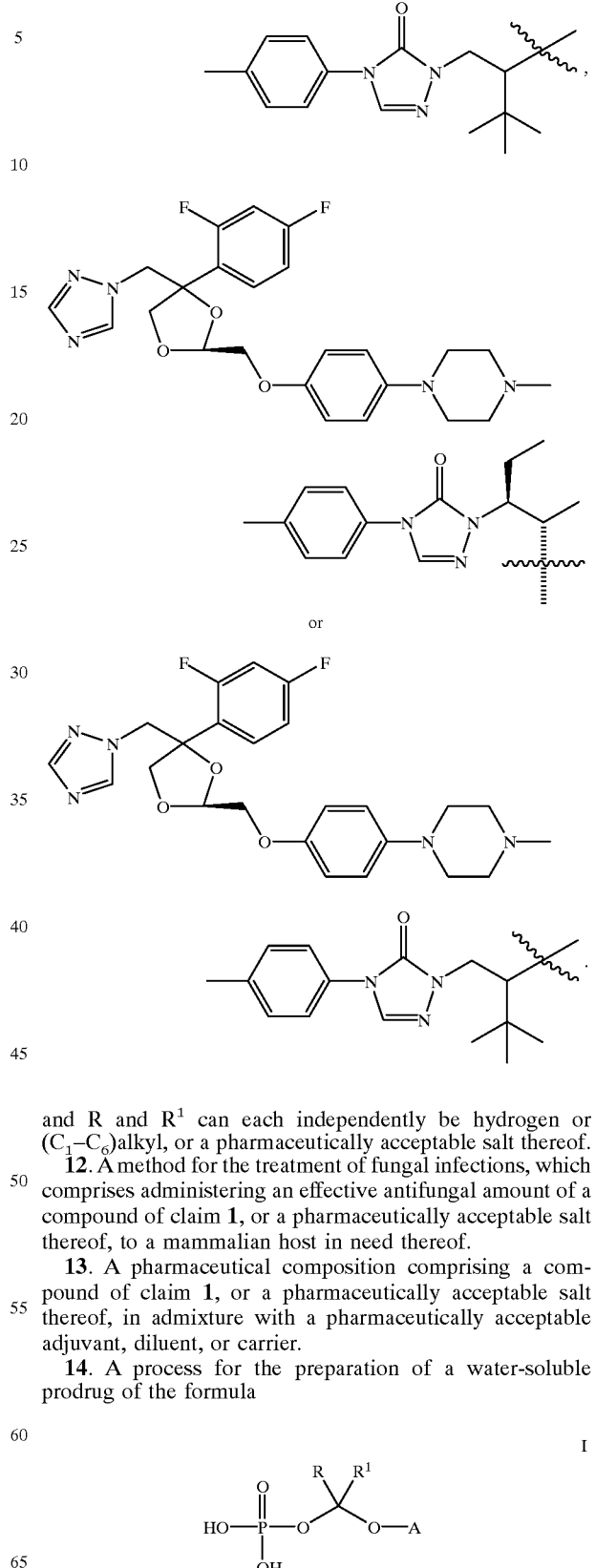

and R and R¹ can each independently be hydrogen or $(C_1-C_6)$alkyl, or a pharmaceutically acceptable salt thereof.

12. A method for the treatment of fungal infections, which comprises administering an effective antifungal amount of a compound of claim 1, or a pharmaceutically acceptable salt thereof, to a mammalian host in need thereof.

13. A pharmaceutical composition comprising a compound of claim 1, or a pharmaceutically acceptable salt thereof, in admixture with a pharmaceutically acceptable adjuvant, diluent, or carrier.

14. A process for the preparation of a water-soluble prodrug of the formula

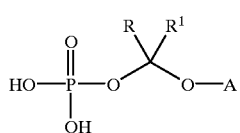

I wherein A is

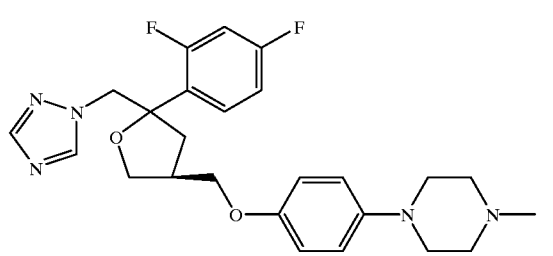

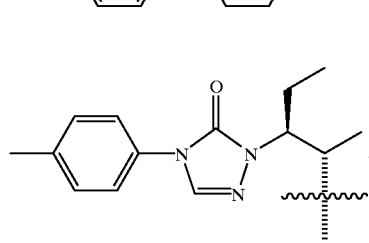

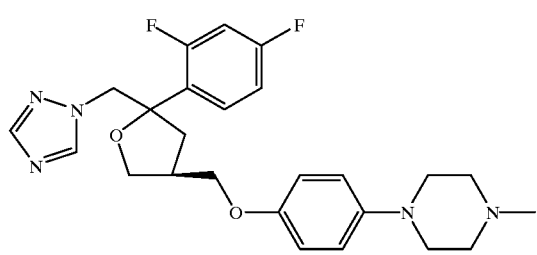

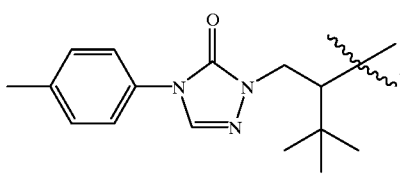

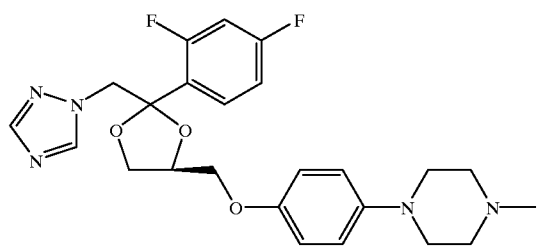

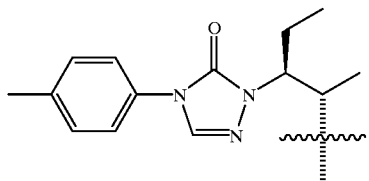

,

-continued

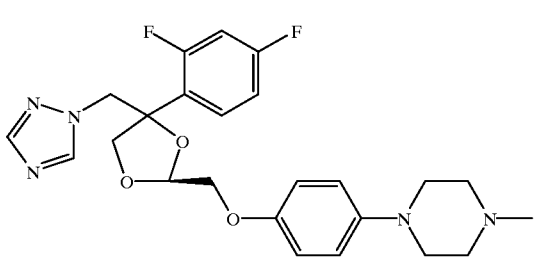

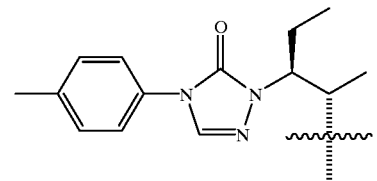

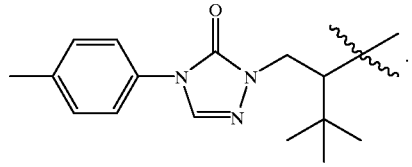

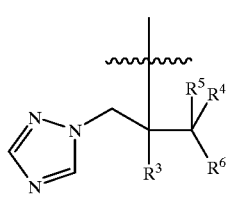

;

or a group of the formula wherein
  R³ represents a phenyl group substituted by one or more halogen atoms;
  R⁴ represents hydrogen or CH₃;
  R⁵ represents hydrogen, or taken together with R⁴ may represent =CH₂;
  R⁶ represents thiazolyl which may be optionally substituted by one or more groups selected from halogen, =O, phenyl substituted by one or more groups selected from CN, (C₆H₄)—OCH₂CF₂CHF₂ and CH=CH—(C₆H₄)—OCH₂CF₂CHF₂, or phenyl substituted by one or more groups selected from halogen and methylpyrazolyl; and R and $R^1$ are each independently hydrogen or $(C_1-C_6)$alkyl, or a pharmaceutically acceptable salt thereof, which comprises (a) reacting a compound of the formula A—OH wherein A is as defined above with a compound of the formula

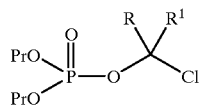

III in which R and $R^1$ are as defined above and Pr represents a hydroxyl-protecting group in an inert organic solvent in the presence of base at a temperature of from about 25° C. to 50° C. to form an intermediate of the formula

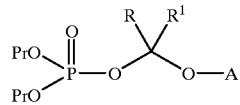

IV wherein Pr, A, R and $R^1$ are as defined above, and (b) removing the protecting groups Pr by conventional means to produce a compound of the formula

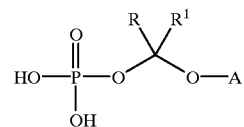

I and, if desired, converting said compound I by conventional means to a pharmaceutically acceptable salt thereof.

15. The process of claim 14 wherein the protecting group Pr is tertiary-butyl.

16. The process of claim 14 wherein the solvent used in Step (a) is tetrahydrofuran.

17. The process of claim 14 wherein the base used in Step (a) is sodium hydride.

18. The process of claim 14 wherein starting material A—OH is

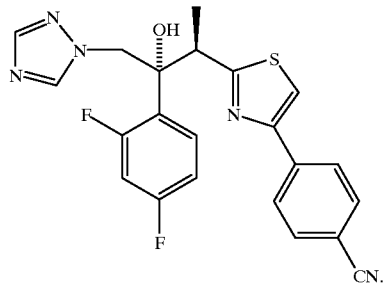

* * * * *

UNITED STATES PATENT AND TRADEMARK OFFICE
CERTIFICATE OF CORRECTION

PATENT NO. : 6,362,172 B2
DATED : March 26, 2002
INVENTOR(S) : Yasutsugu Ueda et al.

It is certified that error appears in the above-identified patent and that said Letters Patent is hereby corrected as shown below:

Column 22,
Line 58, the portion of the claim reading "represents thiazole which may" should read
-- represents thiazole, pyrimidinyl, or triazolyl which for each ring may --;

Column 23,
Line 50,

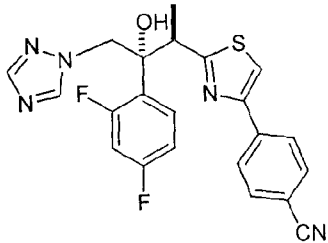 should read 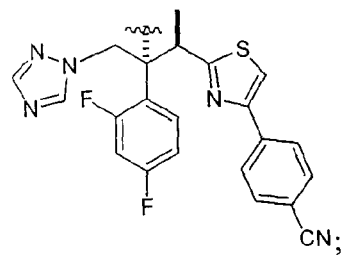

Column 28,
Line 63, the portion of the claim reading "represents thiazole which may" should read
-- represents thiazole, pyrimidinyl, or triazolyl which for each ring may --.

Signed and Sealed this

Seventh Day of October, 2003

JAMES E. ROGAN
*Director of the United States Patent and Trademark Office*

UNITED STATES PATENT AND TRADEMARK OFFICE
CERTIFICATE OF CORRECTION

PATENT NO.        : 6,362,172 B2
APPLICATION NO.   : 09/757438
DATED             : March 26, 2002
INVENTOR(S)       : Yasutsugu Ueda It is certified that error appears in the above-identified patent and that said Letters Patent is hereby corrected as shown below:

Column 23:  Claims 8 & 9 should read.

8.  The crystalline bis lysine salt of (2R,3R)-3-[4-(4-cyanophenyl)thiazol-2-yl]-2-(2,4-difluorophenyl)-1-(1H-1,2,4-triazol-1-yl)-2-[(dihydrogen phosphonoxy ~~phenoxy~~)methoxy]butane.

9.  The crystalline tertiary-butylamine salt of (2R,3R)-3-[4-(4-cyanophenyl)thiazol-2-yl]-2-(2,4-difluorophenyl)-1-(1H-1,2,4-triazol-1-yl)-2-[(dihydrogen phosphonoxy ~~phenoxy~~)methoxy]butane.

Signed and Sealed this

Thirtieth Day of January, 2007

JON W. DUDAS
*Director of the United States Patent and Trademark Office*